United States Patent [19]

Kemp

[11] Patent Number: 4,768,499

[45] Date of Patent: Sep. 6, 1988

[54] BACK AND ABDOMINAL MUSCLE SUPPORTING BELT

[76] Inventor: Kenneth A. Kemp, 21401 Power Rd., Farmington Hills, Mich. 48024

[21] Appl. No.: 15,669

[22] Filed: Feb. 17, 1987

[51] Int. Cl.⁴ ............................................. A61F 5/02
[52] U.S. Cl. ................................... 128/78; 128/96.1; 128/100.1
[58] Field of Search ................... 128/78, 100, 95, 99, 128/68, 69, 95, 96, 102

[56] References Cited

U.S. PATENT DOCUMENTS

| | | | |
|---|---|---|---|
| 3,052,236 | 9/1962 | Schrieber | 128/78 |
| 3,717,143 | 2/1973 | Johnson | 128/78 |
| 4,159,020 | 6/1979 | Soiron et al. | 128/78 |
| 4,522,135 | 11/1985 | Racz | 128/78 |
| 4,545,370 | 10/1985 | Welsh | 128/78 |
| 4,622,957 | 11/1986 | Curlee | 128/78 |

Primary Examiner—Charles Pearson
Assistant Examiner—Huong Q. Pham
Attorney, Agent, or Firm—Charles W. Chandler

[57] ABSTRACT

A back and stomach supporting belt has an unpadded central panel of ¼ inch leather which is placed in the small of the back to cover the five lumbar vertebra and the sacrospinalis muscles on both sides of the lumbar vertebra, but not over the large lower portions of the latissimus dorsi muscles. The ends of the belt extend from the central panel so that when fastened together around the user's abdominal muscles, the central panel bears against the lumbar area, pressing forward into a position restricting the sacrospinalis muscles and the lumbar vertebra from relaxing into a position which may cause pain to the lower part of the spine.

8 Claims, 1 Drawing Sheet

BACK AND ABDOMINAL MUSCLE SUPPORTING BELT

BACKGROUND OF THE INVENTION

This invention is related to a belt having an enlarged, unpadded central panel of ¼ inch leather placed into the small of the user's back so that when the belt ends are connected together around the abdominal muscles, the belt and the abdominal muscles cooperate to support the lumbar vertebrae.

The spinal column or back bone is built up of a series of block-like bones called vertebrae, stacked on top of one another. A single vertebra is a flat, roughly circular bone with rearward projecting knobs to which muscles are attached. Between the vertebrae are pads of elastic cartilage which absorb shocks and permit overlying vertebrae to bend and twist a bit without grating upon each other.

Although the spine is continuous, the curves and certain areas of the spine have special names. The head is carried at the upper end of the cervical or neck region which has seven vertebrae. Below is the thoracic segment of 12 vertebrae which carry the ribs.

The lumbar are is below the thoracic section. There are five large lumbar vertabrae, and the general region is sometimes called the "small of the back". It is a sort of pivot for rocking movements of the upper part of the body upon lower parts and is subjected to concentrated stresses. This is an area of discomfort for many.

The prior art discloses several devices for bringing comfort to this area. For example, U.S. Pat. No. 4,622,957, which issued Nov. 18, 1986 to James D. Curlee, disclsoes a therapeutic corset adapted for the sacrum lumbar and thoracic regions of the body. The corset includes a padded bladder provided with a duct for introducing fluid. The inflated bladder is disposed next to the user for the purpose of "filling" the unique contours of the sacro-lumbar region of the spine by providing a pressure for comfort to specific areas while controlling the overall stability of the thoracic spinal region.

U.S. Pat. No. 3,717,143 which issued Feb. 20, 1973 to Curt H. Johnson, discloses a "Lumbar-Sacral Support". Johnson teaches of a corset for obviating the problems of existing supports which use "relatively rigid non-flexible stays" and cause unequalized and undesired pressure against various regions of the lower torso. Johnson's flexible corset has an enlarged portion carrying a plurality of elongated, vertically extending, laterally spaced stays placed over padding disposed adjacent the inside face of the corset. The padding precludes direct contact between the patient and the prebent stays.

U.S. Pat. No. 4,552,135, which issued Nov. 12, 1985 to Gabor B. Racz, et al, also shows a "Lumbar Belt" with a relatively large rear belt section superimposed over the small of the back, and an air filled chamber disposed between the small of the back and the belt.

SUMMARY OF THE INVENTION

The broad purpose of the present invention is to provide an improved abdominal muscle and back supporting belt formed of a central panel of ¼ inch thick leather. Two end straps of ⅛ inch leather are connected to opposite sides of the central panel such that the two straps can be fastened together around the stomach muscles. The belt and abdominal muscles cooperate to support the lumbar portion of the back. The width and height of the central panel is such that it fits within the recessed portion of the back between the large muscles and over the sacrospinalis muscles which are connected to the lumbar vertebrae.

The central section of the belt is unpadded so that its relatively stiff construction is superimposed over both the lumbar muscles and the lumbar vertebrae to provide a brace which supports both abdominal and back muscles in relative comfort. It provides solid support to a localized section of the lower back. It restricts the lumbar muscles and vertebrae, as the user relaxes into a corrective position. It is less expensive than conventional back-supporting devices. The unpadded leather provides better support than padding or cushioning which permit relative movement between the vertebrae and the back muscles.

The preferred embodiment of the invention can be worn by most individuals who are standing, walking, sitting, running, lying, bending, lifting weights and the like, and may be worn either outside the clothing or inside, whether at work, play or at home. It differs from a weight-lifting belt, which has thicker end straps and a long wide back panel that surrounds the kidney area.

Conventional belts do not take into account the fact that the small of the back is also supported by the abdominal muscles, and thus, because of their design, give little or no support to abdominal muscles. The preferred belt provides better support for the small of the back because it is closely adjacent the lumbar area, whereas conventional belts with a wide central back attachment and a greater length tend to ride up on the large back muscles, away from the spine-supporting muscles. Spongy cushioning materials which fit into the dimples and directly against the spine give little added support because of their conformity to the exact contours of the body. The preferred belt conforms only to the area of the back which contains the spine-supporting muscles.

Further, the end straps of the preferred belt are wide enough to be comfortable but firm enough to help support weak abdominal muscles. Weak abdominal muscles are a constributing factor in many cases of back pain.

Still further objects and advantages of the present invention will become readily apparent in those skilled in the art to which the invention pertains upon reference to the following detailed description.

DESCRIPTION OF THE DRAWING

The description refers to the accompanying drawing in which like reference characters refer to like parts throughout the several views, and in which.

DESCRIPTION OF THE PREFERRED EMBODIMENT

Figure 1:
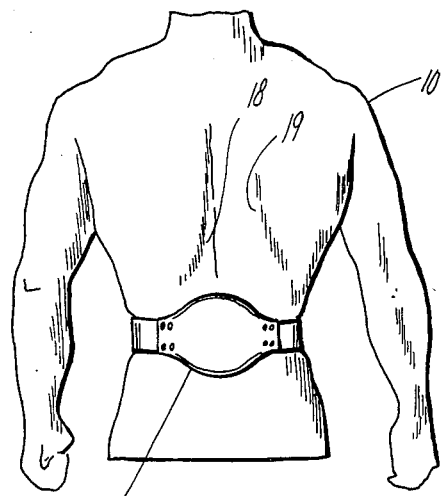
FIG. 1 is the back view of a user with the central panel of the preferred belt mounted over the small of the back.
Figure 2:
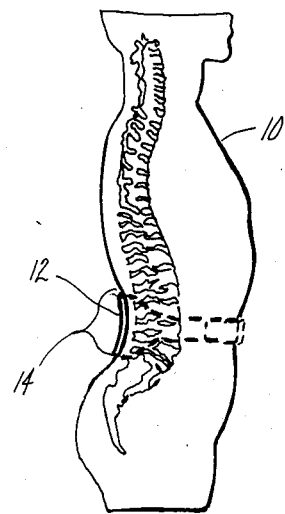
FIG. 2 is a sectional view showing the position of the central panel with respect to the lumbar area of the back.

Referring to the drawing, FIGS. 1 and 2 illustrate user 10 wearing a belt 12 illustrating the preferred embodiment of the invention. The user has a conventional spine including a lumbar area 14 covering the five lumbar vertebrae. Sacrospinalis muscles are connected to the lumbar vertebrae in what is known "as the small of the back". This lumbar area is disposed in a recess below what is known as the latissimus dorsi muscles which are outlined at 18 and 19 in FIG. 1. These are larger muscles than the sacrospinalis muscles.

Figure 3:
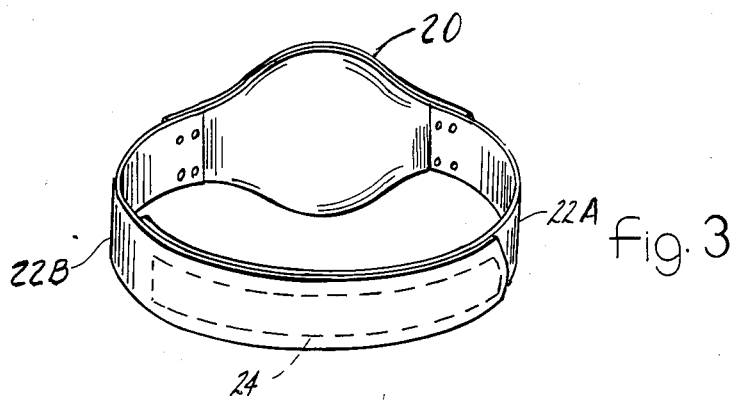
FIG. 3 is a view of the preferred belt with its ends fastened together.
Figure 4:
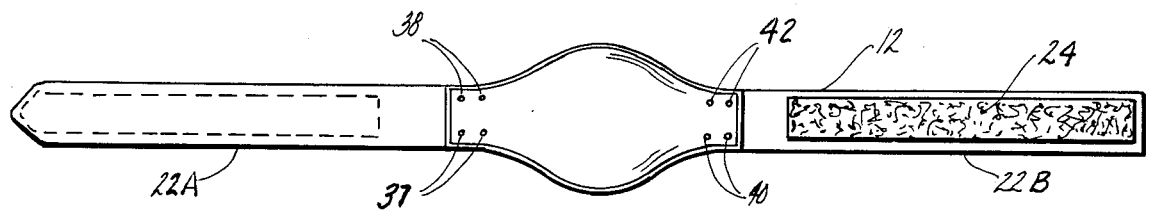
FIG. 4 is a view of the preferred belt with its ends extended.
Figure 5:
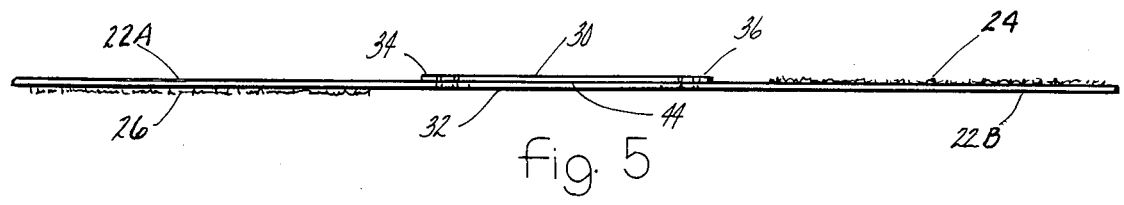
FIG. 5 is a view showing the edge view of the belt.

Referring to FIGS. 3 to 5, belt 12 comprises three sections including a central panel 20 and a pair of end straps 22A and 22B. Central panel 20 and straps 22A and 22B are preferably formed of leather. A fabric, hook fastener strip 24 is connected along the major length of strap 22B while a complementary fabric loop fastener section 26 is attached to the opposite side of strap section 22A. Hook and loop fastener means 24 and 26 permit the user to releaseably fasten the belt around the major portion of his abdominal muscles.

Straps 22A and 22B are preferably each formed of ⅛ inch thick leather 2-½ inches wide. The central panel has a somewhat oval shape with a maximum width for, illustrative purposes, of about 6 inches. The central panel is formed of a pair of ⅛ inch thick leather sections 30 and 32, superimposed over one another. Section 30 has a pair of ends 34 and 36 which extend beyond the sides of section 32 and overlap the ends of the two straps. Rivet means 37 and 38; connect one end of strap 22A to end 34 of central section 30, while the opposite end of central section 30 is attached by rivets 40 and 42 to the end of strap 22B.

Adhesive means 44 is disposed between the two central sections 30 and 32 to fasten them together to form a single central panel, and between section 30 and the overlapped ends of the two straps.

In use, the belt is mounted with central panel 20 disposed in the small of the back over the five lumbar vertebrae, below the latissimus dorsi muscles. The straps are then attached together around the user's abdominal muscles with sufficient pressure to force the central panel, as illustrated in FIGS. 1 and 2, against the sacrospinalis muscles and the five lumbar vertebrae into a supported position so that the belt cooperates with the abdominal muscles to brace the lumbar are of the spine.

Having described my invention, I claim:

1. A back and abdominal muscle supporting belt adapted to be releaseably placed around a user's back and abdominal muscles including:
   a pair of elongated flexible straps;
   an uncushioned central panel connected between the pair of staps and means for releasably connecting the straps together;
   the central panel having an inside surface of a relatively stiff, leather-like material, and a thickness greater than the thickness of the straps, the straps having a width less than the width of the central panel such that the central panel is entirely receivable within the small of the back over both the lumbar area of the back and a portion of the sacrospinalis muscles, but not over the larger portion of the latissimus dorsi muscles such that when the straps are fastened together around the user, the uncushioned central panel is received within the small of the back and the belt cooperates with the user's abdominal muscles to brace the lumbar vertebrae.

2. A combination as defined in claim 1, in which the central panel is formed of about ¼ inch thick leather, and the straps are formed of about ⅛ inch thick leather.

3. A combination as defined in claim 2, in which the central panel is formed of two superimposed sections of about ⅛ inch thick leather.

4. A combination as defined in claim 1, in which the means connecting the straps together comprises a pair of cooperating sections of hook and loop fasteners.

5. A combination as defined in claim 1, in which the central panel has a generally oval configurations.

6. A combination as defined in claim 2, in which the central panel is about 6 inches in width and the straps are about 2-½ inches in width.

7. A combination as defined in claim 1, including rivet means for connecting the two straps to the central panel.

8. A belt as defined in claim 1, in which the central panel is formed of two superimposed sections of leather, each having a generally oval configuration, and the straps are each formed of a single section of leather.

* * * * *